(12) United States Patent
Fugiel et al.

(10) Patent No.: US 8,716,181 B2
(45) Date of Patent: *May 6, 2014

(54) SEED GERMINATION ACCELERATION

(75) Inventors: Judith Fugiel, Lake Villa, IL (US); Peter D. Petracek, Grayslake, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1257 days.

This patent is subject to a terminal disclaimer.

(21) Appl. No.: 12/214,561

(22) Filed: Jun. 20, 2008

(65) Prior Publication Data

US 2008/0318789 A1 Dec. 25, 2008

Related U.S. Application Data

(60) Provisional application No. 60/936,389, filed on Jun. 20, 2007.

(51) Int. Cl.
*A01N 25/26* (2006.01)
*A01N 43/08* (2006.01)
*A01P 21/00* (2006.01)
*A01N 43/02* (2006.01)

(52) U.S. Cl.
USPC ............ 504/100; 504/101; 504/140; 504/297

(58) Field of Classification Search
USPC .......................... 504/296, 100, 297, 101, 140
See application file for complete search history.

(56) References Cited

U.S. PATENT DOCUMENTS

| | | |
|---|---|---|
| 4,110,102 A | 8/1978 | Pharis |
| 4,749,402 A * | 6/1988 | Garrett et al. ............... 71/28 |
| 5,532,206 A | 7/1996 | Evans et al. |
| 6,100,219 A | 8/2000 | Sakai et al. |
| 2002/0039971 A1 | 4/2002 | Hayashi et al. |

FOREIGN PATENT DOCUMENTS

| | | |
|---|---|---|
| GB | 1 583 702 | 1/1981 |
| WO | WO 2005/115142 | 12/2005 |

OTHER PUBLICATIONS

Ho, Rong, Optimum Timing of Gibberellin A4/7 Sprays to Promote Cone Production in Jack Pine Seedlings, 1994, New Forests, vol. 8, pp. 61-69.*
Renard, H.A., Breaking Dormancy with Gibberellins in Four Species: *Impatients balsamina, Lavandula angustifolia, Brassica rapa*, and *Viola odorata*, 1978, Seed Science and Technology, vol. 6, Issue 3, Abstract retrieved from STN.*
Chadoeuf, R., Survival of Buried Seeds of Interspecific Hybrids between Oilseed Rape, Hoary Mustard, and Wild Radish, 1998, Field Crops Research, vol. 58, pp. 197-204.*
Emongor, V., Effect of Promalin on Growth and Development of Kale (*Brassica oleracea* L. Var. Acephala DC), 2004, Journal of Agronomy, vol. 3, Issue 3, pp. 208-214.*
Holdsworth, M., Genetic Control Mechanisms Regulating the Initiation of Germination, 2001, Journal of Plant Physiology, vol. 158, pp. 439-445.*
Brassicaceae Article, Encyclopedia Britannica, 2011 [retrieved on May 11, 2011]. retrieved from Internet <URL:http://www.britannica.com/EBchecked/topic/77928/Brassicaceae?sections=77928>, p. 1.*
Auer, C.A. Cytokinin Inhibition of *Arabidopsis* Root Growth: An Examination of Genotype, Cytokinin Activity, and N6-Benzyladenine Metabolism, 1996, Journal of Plant Growth Regulation, vol. 15, pp. 201-206.*
EP Search Report ssued Mar. 22, 2012.
Emongor et al., Effect of promalin on growth and development of kale (*Brassica oleracea* L. Vaqr. Acephala DC), Journal of Agronomy, Asian Network of Scientific Information, vol. 3, No. 3, Jan. 1, 2004 pp. 208-214, XP009156847.
Holdsworth et al., "Genetic control mechanisms regulating the initiation of germination", Journal of Plant Physiology, Fischer, Stuttgart, De, Jan. 1, 2001, pp. 439-445, XP004955039.

* cited by examiner

*Primary Examiner* — John Pak
*Assistant Examiner* — Andriae M Holt
(74) *Attorney, Agent, or Firm* — Wood, Philips, Katz, Clark & Mortimer

(57) ABSTRACT

The present invention is generally directed to the use of gibberellin 4/7 (GA4/7) in the field of seed treatment, specifically to accelerate crop germination.

2 Claims, No Drawings

SEED GERMINATION ACCELERATION

FIELD OF THE INVENTION

The present invention generally relates to the field of seed treatment. More specifically, the invention relates to the use of gibberellin 4/7 (GA4/7) to accelerate germination of canola and rapeseed.

BACKGROUND OF THE INVENTION

In the commercial production of crops it is desirable to be able to plant seeds early. For example, early planting of seed crops during sub-optimal cold soil temperatures may allow farmers to improve yields by extending the growing season (Lawton, *Progressive Farmer*, April 2007: B-1 to B-3) and help manage a busy planting schedule. Also, early planting may permit the planting of warmer growing zone varieties of crops. However, currently, minimum germination temperatures limit crop establishment in early spring and require many seeds to be planted later in the season. A seed treatment that would promote cold temperature germination would be useful.

Seed priming has been used to accelerate cold temperature germination. However, priming requires the seed to be exposed to water for a period of time. Also, the process of priming requires a large facility and is not readily useable for large crops.

Therefore, there is a need in the art for an alternative to seed priming. Application of a seed treatment can be logistically simpler and more flexible in allowing a range of chemical treatments that produce different physiological effects, depending on the crop, active ingredient and rate of application.

SUMMARY OF THE INVENTION

The present invention is generally directed to the treatment of seeds, for example, canola and rapeseed, with GA4/7 to accelerate low temperature germination. This invention would permit the planting of longer season varieties of crops in cold growing regions. This invention would also permit the more rapid establishment of crops in early spring thus allowing for earlier canopy closure and growth during the wet season, and increased yield. This invention would also permit a greater period for planting thus allowing more flexibility in managing the planting date.

DETAILED DESCRIPTION OF THE INVENTION

In one embodiment, the present invention generally relates to seed treatment formulations suitable for accelerating crop germination comprising an effective amount of GA4/7. In a preferred embodiment, said crops are canola and rapeseed. In another preferred embodiment, said crops are members of the Brassicaceae family.

The effective amount of GA4/7 is an amount of GA4/7, the application of which results in acceleration of crop germination as compared to crop germination in the absence of GA4/7. The effective amount can vary depending on the crop and is generally in the range of about 0.1 ppm to about 10,000 ppm, more preferably from about 0.5 ppm to about 500 ppm, and most preferably from about 5 ppm to about 50 ppm. It is well within a skill of a person of ordinary skill in the art to determine an effective amount of GA4/7 for a specific crop.

In another embodiment, the present invention generally relates to methods of accelerating crop germination comprising applying to crops an effective amount of GA4/7.

For the purposes of this Application, GA4/7 is defined as mixture of GA4 ((1α,2β,4aα,4bβ,10β)-2,4a-dihydroxy-1-methyl-8-methylenegibb-1,10-dicarboxylic acid 1,4a-lactone) and GA7 ((1α,2β,4aα,4bβ,10β)-2,4a,7-trihydroxy-1-methyl-8-methylenegibb-1,10-dicarboxylic acid 1,4a-lactone); GA3 (gibberellic acid) is defined as (1α,2β,4aα,4bβ,10β)-2,4a,7-trihydroxy-1-methyl-8-methylenegibb-3-ene-1,10-dicarboxylic acid 1,4a-lactone; 6BA ($N^6$-benzyladenine) is defined as $N^6$-phenylmethyl)-1H-purin-6-amine; and CPPU (forchlorfenuron) is defined as 1-(2-chloro-4-pyridyl)-3-phenylurea.

Surprisingly and unexpectedly, Applicants have discovered that applying GA4/7 to canola seeds significantly increased the percent of early germination as compared to applying GA3, 6BA, and CPPU.

In an embodiment of the present invention, the seeds are treated with solutions comprising GA4/7. The amount of the solutions should be enough to wet the seeds. Techniques of seed treatment application are well known to those skilled in the art, and they may be readily used in the context of the present invention. The compositions of the present invention may be applied as a slurry or soak. Film coating and encapsulation may also be used. The coating processes are well known in the art and employ the techniques of film coating, encapsulation, immersion, etc. The methods of application of the compositions of the present invention may be varied, and the invention is intended to include any technique that is to be used by one of skill in the art.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

Throughout the application, the singular forms "a," "an," and "the" include plural reference unless the context clearly dictates otherwise.

The following examples are intended to illustrate the present invention and to teach one of ordinary skill in the art how to make and use the invention. They are not intended to be limiting in any way.

For all seed treatments, 1 ppm active ingredient refers to 1 microgram active ingredient per gram of seed. For these studies, GA3, GA4/7, 6BA or CPPU were each dispensed into a 15 ml centrifuge tube, and 2.5 ml of de-ionized water was then added to each tube. The solution was mixed on a vortex mixer and 0.015 ml of this solution was then placed in another 15 ml. centrifuge tube along with 0.6 grams of canola seeds (cv. Westar). Seeds were mixed by rotating 360° on a Labquake Rotisserie for 30 minutes. To simulate commercial seed treatments, the amount of solutions was just sufficient to wet the seeds. After treating, the seeds were placed in weigh boats for overnight drying.

Petri plate studies: Each standard petri plate (100 mm×50 mm) contained 1 blue Anchor germination circle (3¼ inches in diameter) drenched with 8 ml of de-ionized water cooled to 6° C. Each treatment consisted of 3 petri plates of 15 seeds each. After plating, the petri plates were placed in a Nalgene plastic container pre-cooled to 6° C. The plastic container containing the petri plates was placed in a growth chamber at 6° C. with a 16-hour light cycle for the duration of the study. Seeds were visually observed daily for germination as determined by emergence of root from the seed coat.

EXAMPLE

Canola seeds (cv. Westar) were treated with solutions containing GA4/7, GA3, 6BA, or CPPU. The solutions were sufficient only to wet the seeds. The amount of applied GA4/7 (0.5, or 50 ppm), GA3 (0.5, 5 or 50 ppm), 6BA (5 or 50 ppm), or CPPU (5 or 50 ppm) is expressed as ppm or micrograms of compound per gram of seed. GA4/7 at 5 ppm surprisingly increased the percent of early germination more than GA3, 6BA, or CPPU at 50 ppm (Table 1).

TABLE 1

Effect of GA3, GA4/7, 6BA, or CPPU seed treatments on germination of canola (cv. Westar) seed in petri plates at 6° C. at day 5, 6, and 7 after treatment (n = 3 replicate plates of 15 seeds).

|  | Percent germinated | | |
| --- | --- | --- | --- |
|  | Day 5 | Day 6 | Day 7 |
| Control | 0 | 0.3 | 0.3 |
| GA4/7 0.5 ppm | 0 | 0.3 | 0.7 |
| GA4/7 5 ppm | 1.7 | 6.0 | 11.7 |
| GA4/7 50 ppm | 4.5 | 11.5 | 14.0 |
| GA3 0.5 ppm | 0 | 0.3 | 0.3 |
| GA3 5 ppm | 0 | 0.3 | 0.7 |
| GA3 50 ppm | 0.3 | 2.7 | 5.0 |
| 6BA 5 ppm | 0 | 0 | 0 |
| 6BA 50 ppm | 0 | 0.3 | 0.3 |
| CPPU 5 ppm | 0 | 0 | 0.3 |
| CPPU 50 ppm | 0 | 0 | 0 |

The invention claimed is:

1. A method of accelerating germination or increasing crop yield in canola or rapeseed comprising applying to the seeds of said canola or rapeseed from 5 ppm to 50 ppm.

2. The method of claim 1, wherein said gibberellin 4/7 is combined with other agrochemicals.

* * * * *